US008957392B2

(12) United States Patent  
Iwasaki

(10) Patent No.: US 8,957,392 B2  
(45) Date of Patent: Feb. 17, 2015

(54) MASS SPECTROMETER

(71) Applicant: Canon Kabushiki Kaisha, Tokyo (JP)

(72) Inventor: Kota Iwasaki, Atsugi (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 14/349,892

(22) PCT Filed: Oct. 10, 2012

(86) PCT No.: PCT/JP2012/076743  
§ 371 (c)(1),  
(2) Date: Apr. 4, 2014

(87) PCT Pub. No.: WO2013/054937  
PCT Pub. Date: Apr. 18, 2013

(65) Prior Publication Data  
US 2014/0239173 A1 Aug. 28, 2014

(30) Foreign Application Priority Data

Oct. 13, 2011 (JP) ................................. 2011-225509  
Oct. 5, 2012 (JP) ................................. 2012-223084

(51) Int. Cl.  
H01J 49/06 (2006.01)  
H01J 49/00 (2006.01)  
H01J 49/26 (2006.01)  
B01D 59/44 (2006.01)  
H01J 49/14 (2006.01)  
H01J 49/40 (2006.01)

(52) U.S. Cl.  
CPC ............ H01J 49/061 (2013.01); H01J 49/142 (2013.01); H01J 49/0031 (2013.01); H01J 49/40 (2013.01)  
USPC ........ 250/396 R; 250/281; 250/282; 250/283; 250/288; 250/397

(58) Field of Classification Search  
CPC ............ H01J 2237/31749; H01J 37/08; H01J 2237/28; H01J 49/061; H01J 2237/2527  
USPC .............. 250/281, 282, 283, 288, 396 R, 397  
See application file for complete search history.

(56) References Cited

U.S. PATENT DOCUMENTS

| | | | |
|---|---|---|---|
| 5,086,227 A * | 2/1992 | Toita et al. | 850/43 |
| 6,888,129 B2 | 5/2005 | Bowdler et al. | |
| 6,900,447 B2 * | 5/2005 | Gerlach et al. | 250/494.1 |
| 7,041,970 B2 | 5/2006 | Bowdler et al. | |
| 8,759,756 B2 * | 6/2014 | Iwasaki | 250/287 |

* cited by examiner

FOREIGN PATENT DOCUMENTS

| | | |
|---|---|---|
| JP | 3-78951 A | 4/1991 |
| JP | 4-334857 A | 11/1992 |
| JP | 5-129000 A | 5/1993 |
| JP | 7-29535 A | 1/1995 |
| JP | 8-153484 A | 6/1996 |
| JP | 2001-141673 A | 5/2001 |
| JP | 2002-141016 A | 5/2002 |
| WO | 2013/073373 A1 | 5/2013 |

OTHER PUBLICATIONS

A. Benninghoven et al., Secondary Ion Mass Spectrometry: Basic Concepts, Instrumental Aspects, Applications, and Trends, pp. 926-927 (Wiley, New York, 1987).

*Primary Examiner* — Nikita Wells  
(74) *Attorney, Agent, or Firm* — Fitzpatrick, Cella, Harper & Scinto

(57) ABSTRACT

In order to solve a problem in a mass spectrometry that a distribution of an emitted ion and a substance distribution on the measurement object surface are different from each other, which is due to a shaded portion of a irregular surface which falls under a shadow of primary beam, a primary ion optical system of the present apparatus includes a deflection unit configured to deflect the primary ion in such a manner that the primary ion intersects a flight space of the secondary ion in the course of flight.

31 Claims, 8 Drawing Sheets

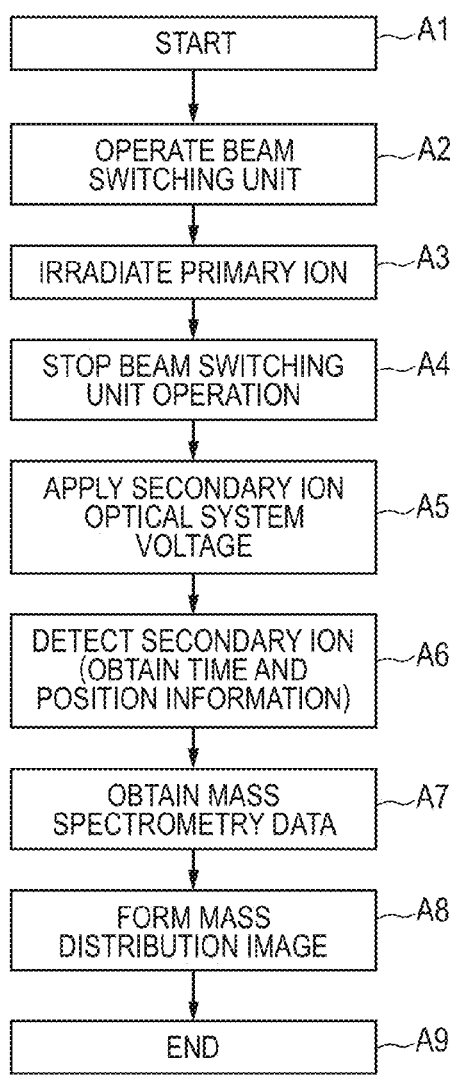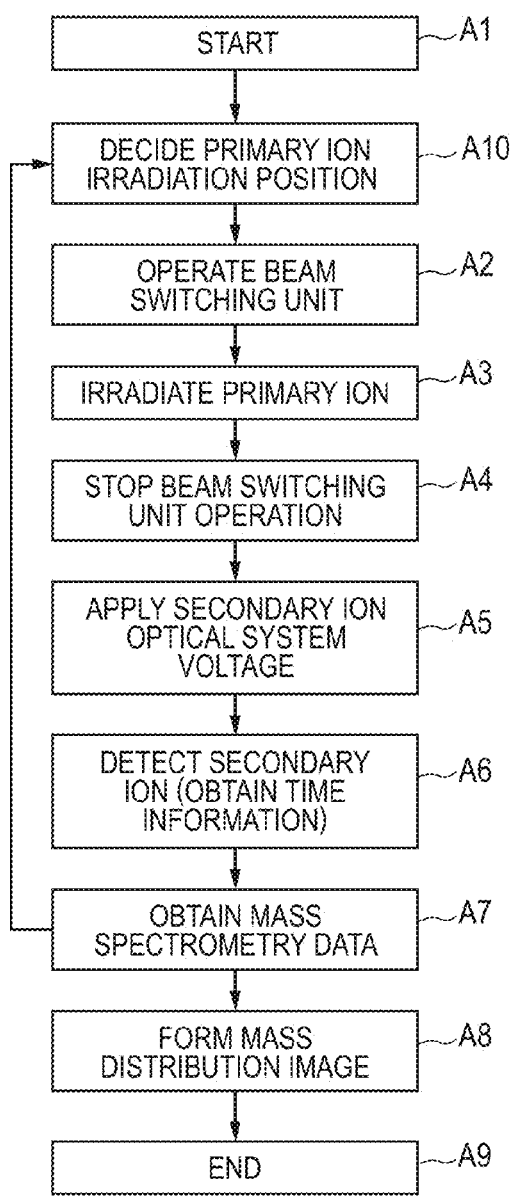

MASS SPECTROMETER

TECHNICAL FIELD

The present invention relates to a mass spectrometer which performs mass spectrometry by ionizing at least a part of a measurement object and measuring the ion.

BACKGROUND ART

As a method for detecting a substance distribution on a measurement object surface particularly in the field of pathology research and drug development, "imaging mass spectrometry" has recently been attracting attention. The imaging mass spectrometry is a method of obtaining distribution information of a substance on a surface of a measurement object by performing two-dimensional mass spectrometry of the surface of the measurement object and obtaining a two-dimensional distribution of detected intensity of the substance corresponding to a mass-to-charge ratio. With the imaging mass spectrometry, it is possible to identify a biological molecule such as protein, a drug molecule, and the like and to measure a spatial distribution of the molecule with high spatial resolution.

A mass spectrometry, in general, is a method of ionizing a sample by irradiating the sample with laser light, an ion, an electron, or the like and separating the ionized sample by the mass-to-charge ratio, to thereby obtain a spectrum formed of a mass-to-charge ratio and detected intensity thereof.

As a unit for generating an ion from a measurement object, charged particle beams such as a laser beam and an ion beam (hereinafter collectively referred to as a primary beam) are usable. In the case where the primary beam is the ion beam, the emitted ion is called a secondary ion. As examples of using the laser as the primary beam, a matrix-aided laser desorption ionization (MALDI) for attaining the ionization by irradiating a sample, which being blended with a matrix and crystallized, with pulsed and finely focused laser light, and secondary ion mass spectrometry (SIMS) for attaining ionization by irradiating a sample with a primary ion beam, have been known.

As a method for separating the ionized sample by a mass-to-charge ratio and detecting the sample, a time-of-flight type which is suitable for detecting a molecule having a large mass, such as a protein, is often adopted to the imaging mass spectrometry. In a time-of-flight mass spectrometer, an ion is emitted from a surface of a measurement object in a pulsed manner, and the ion is accelerated in vacuum by an electric field. Since flight speeds of ions are each different depending on its mass-to-charge ratio, the mass-to-charge ratio of the target ion can be measured by measuring a time required for the target ion to fly a certain distance from the measurement object to a detection device.

Also, the imaging mass spectrometry includes two methods, namely, a scanning type and a projection type.

The scanning type is a method including sequentially performing mass spectrometry of fine areas (depends on a beam diameter of a primary beam) on a measurement object and re-constructing a distribution of a substance from results of the mass spectrometry and position information of the fine areas.

In the projection type, a measurement object of a wide area is ionized by irradiating an entire surface of the measurement object with a primary beam having a relatively wide irradiation area, and a time required for a generated ion to arrive at a detection device and a position of arrival of the ion on a surface of the detection device are measured by a position/time sensitive detector. With such configuration, it is possible to measure a spatial distribution of a substance contained in the measurement object by simultaneously detecting a mass of the detected ion and a position of the ion on the surface of the measurement object.

As a representative mass spectrometer, the one using laser light as the primary beam (PTL 1) and the one using an ion beam (PTL 2) have been disclosed.

CITATION LIST

Patent Literature

PTL 1: Japanese Patent Application Laid-Open No. 2002-141016

PTL 2: Japanese Patent Application Laid-Open No. 2001-141673

SUMMARY OF INVENTION

Technical Problem

In the conventional mass spectrometers, in many cases both in the scanning type and the projection type, the primary beam is so formed as to be made obliquely incident to a surface of a measurement object. This is because it is necessary to dispose an ion detection system perpendicularly to the surface of the measurement object in order to improve ion capture efficiency. When the primary beam is perpendicularly incident, a primary beam irradiation system interferes with the detection system which detects an ion emitted from the measurement object, and therefore such configuration has difficulty in perpendicularly irradiating the primary beam.

When the primary beam is made obliquely incident on the surface of the measurement object, in the case where the measurement object surface has an irregular height range (hereinafter referred to as an irregularity), a shaded portion which falls under the shadow of the primary beam is emitted on the surface of the measurement object. The shaded portion is not irradiated with the primary beam, and the secondary ion is not emitted from the shaded portion. Therefore, there has been a problem of causing a difference between a spatial distribution of the ion emitted from the sample and a spatial distribution of a substance on a measurement object surface.

In the mass spectrometer described in PTL 1, an optical mirror is provided in an electrode forming an ion detection system, and a laser which enters from the outside of the ion detection system is reflected at the inside of the ion detection system to be made incident to a measurement object. However, it is difficult to adopt the configuration to the case of using the ion beam as the primary beam.

Further, since an ion optical axis of a primary beam and an ion optical axis of an ion detection system are different from each other in the configuration of PTL 1, the ion detection system is disposed obliquely to a measurement object surface when the primary beam is perpendicularly irradiated onto the surface to raise concerns about a deterioration of ion detection efficiency.

Also, in the mass spectrometer described in PTL 2, a primary beam transmission aperture is provided in an ion detector to enable an arrangement in which an ion optical axis of the primary beam and an ion optical axis of an ion detection system are coaxial. However, there are problems that detection efficiency of the ion detector is deteriorated due to the transmission aperture and that it is difficult to adopt the configuration to a projection type secondary ion optical system since the transmission aperture is a blind spot when detecting an ion emitted in an ion optical axis direction.

Solution to Problem

The present invention solves the problems of the conventional technologies.

In view of the above-mentioned problems, a mass spectrometer according to the present invention includes: a platform on which a measurement object is placed; a primary ion source configured to generate a primary ion; a primary ion optical system configured to guide the primary ion to the measurement object and irradiate the measurement object with the primary ion; a detection unit configured to detect a secondary ion emitted from the measurement object; and a secondary ion optical system configured to guide the secondary ion to the detection unit; in which the primary ion optical system includes a deflection unit configured to deflect the primary ion in such a manner that the primary ion intersects a flight space of the secondary ion in the course of flight.

Advantageous Effects of Invention

According to a time-of-flight mass spectrometer of the present invention, surface analysis in a state where influence of irregularity of a measurement object surface is suppressed is enabled. Particularly, since perpendicular incidence is enabled in a configuration in which a path connected to a detector is perpendicular to the measurement object surface, a surface state of a measurement object is detected with high accuracy.

Also, since the mass spectrometer has a primary ion optical system which irradiates a measurement object with a primary ion and a secondary ion optical system which guides an ion from the measurement object to the detector; the primary ion generator is disposed outside an ion optical axis of the secondary ion optical system; and a deflection unit which deflects a trajectory of the primary ion is disposed between the measurement object and the detector, the primary ion optical system and the secondary ion optical system can be coaxially disposed without interference, and the primary ion can be made perpendicularly incident to the measurement object surface. As a result, even in the case where the measurement object surface has an irregularity, the entire surface is irradiated with the primary ion to improve a difference between a distribution of an ion emitted from a sample and a distribution of a substance on the measurement object surface, thereby attaining improvement in measurement accuracy.

Further features of the present invention will become apparent from the following description of exemplary embodiments with reference to the attached drawings.

BRIEF DESCRIPTION OF DRAWINGS

FIG. 4A is a flowchart showing a projection type imaging mass spectrometry.

FIG. 4B is a flowchart showing a scanning type mass spectrometry.

DESCRIPTION OF EMBODIMENTS

Figure 1A:
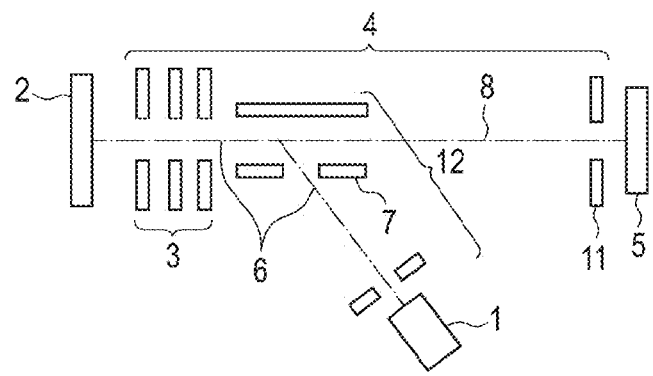
FIG. 1A is a schematic diagram showing a time-of-flight mass spectrometer according to the present invention.

The present invention relates to a mass spectrometer which irradiates a measurement object with primary ion to generate secondary ion therefrom, and detects the secondary ion. FIG. 1A shows one mode of embodiment of a time-of-flight type mass spectrometer according to the present invention. Although the time-of-flight type mass spectrometer is exemplary disclosed herein, the description is not intended to limit the scope of the present invention to the time-of-flight type. The present invention can be applied also to other types, such as ion-trap type or Quadrupole type of mass spectrometers.

The time-of-flight mass spectrometer has a primary ion source 1 which generates a primary ion, a platform 2 on which a measurement object is placed, a primary ion optical system 12 which irradiates the measurement object with the primary ion, a secondary ion optical system 4 as a convergence unit which guides the secondary ion to a detector, detector 5 which is a detection unit to detect the secondary ion, and a not-shown evacuation system and a data processing system. The primary ion optical system 12 has a deflection unit 7 which deflects the primary ion so that the primary ion intersects a flight space of the secondary ion in the course of the flight. The secondary ion optical system 4 has an extraction/projection electrode 3 which is a directing unit which causes a secondary ion emitted from the measurement object to fly and directs the secondary ion to the detection unit, and a deflection unit 7. With such configuration, a part between the deflection unit 7 and the measurement object 2 functions as an ion optical system for both of the primary ion and the secondary ion. The extraction/projection electrode 3 which is the directing unit may preferably be disposed in such a manner as to enclose a flight space of the secondary ion, so that a configuration in which the primary ion is deflected by the deflection unit to fly from the outside of the flight space to the inside of the flight space is preferably achieved. The flight space of the secondary ion herein refers to a space between the measurement object and the detection unit, where the secondary ion flies therethrough.

The primary ion source 1 may be an electron collision type, a surface ionization type, or a liquid metal type ion source and it may preferably be capable of high speed pulse driving at a pulse width of about a several nanoseconds.

Figure 1B:
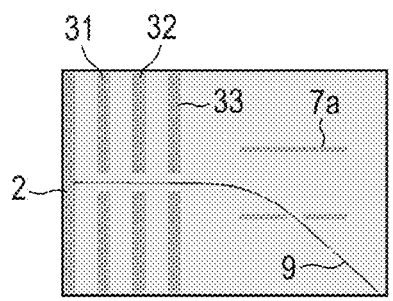
FIG. 1B is a simulation result showing primary ion trajectories according to a first embodiment.
Figure 2A:
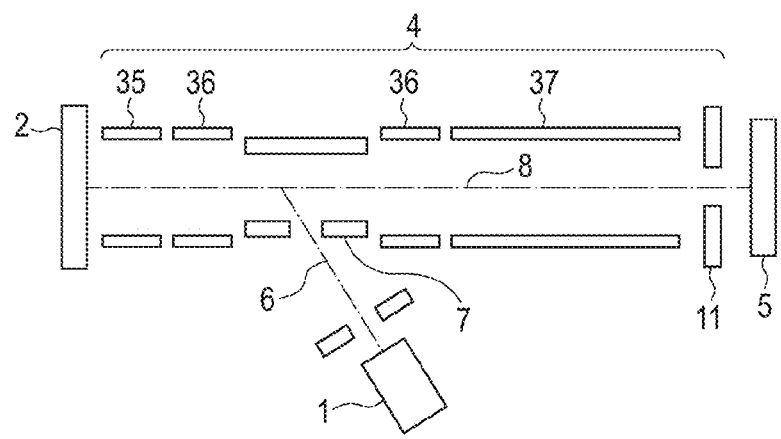
FIG. 2A is a diagram showing a time-of-flight mass spectrometer according to a second embodiment.

A trajectory of the primary ion generated from the primary ion source 1 is deflected by the deflection unit 7 disposed along an ion optical axis of the secondary ion optical system 8 (FIG. 1B). The deflection unit 7 is disposed between the measurement object 2 and the detector 5. It may be disposed between the extraction/projection electrode 3 and the detector 5 as shown in FIG. 1A or among an electrode group for converging the secondary ion as shown in FIG. 2A.

Figure 1C:
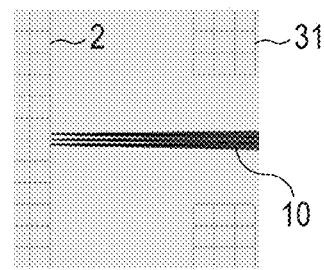
FIG. 1C is a simulation result showing secondary ion trajectories in the vicinity of a measurement object 2 according to the first embodiment.

The deflection unit 7 spatially overlaps with a path of the secondary ion and it has a structure of allowing the secondary ion to transmit at a finite probability (i.e. of switching between the beams) at least when the primary ion does not pass through the deflection unit 7 (FIG. 1C).

Figure 3A:
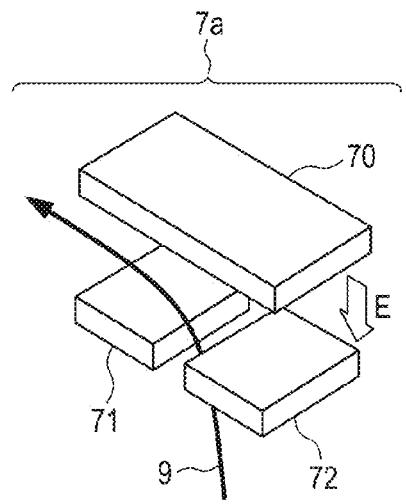
FIG. 3A is a schematic diagram showing a deflection unit according to the first and second embodiments.
Figure 3B:
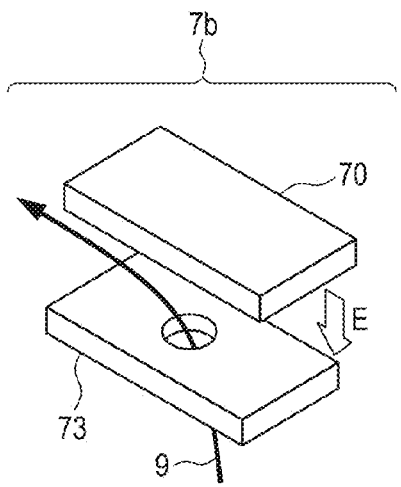
FIG. 3B is a schematic diagram showing a deflection unit having a reference electrode with an aperture.
Figure 3C:
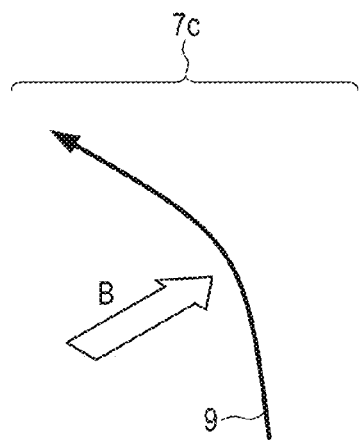
FIG. 3C is a schematic diagram showing a deflection unit of a magnetic field type.
Figure 3D:
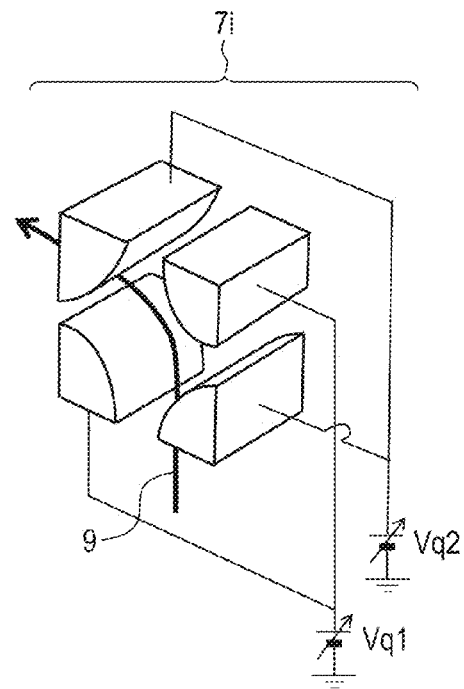
FIG. 3D is a schematic diagram showing a deflection unit of a quadrupolar electric field type.

In the deflection unit 7, two or more electrodes are disposed in such a manner that the secondary ion optical system is disposed therebetween, so that the trajectory of the primary ion is electrostatically deflected by an electric field generated between at least a pair of electrodes which are opposed to each other with the secondary ion optical system being disposed therebetween (FIG. 3A, FIG. 3B and FIG. 3D). A system of deflecting the primary ion trajectory with a Lorentz force by applying a magnetic field as shown in FIG. 3C may also be employed, while the above-described electrostatic deflection unit has a high operation speed and, therefore, advantageous for performing secondary ion mass spectrometry.

When an electrode having a single or a plurality of aperture(s) or a mesh which allows the secondary ion to pass therethrough is used, a penetration type deflection unit in which the secondary ion optical axis is not formed between the electrodes may be provided (FIG. 6A, FIG. 6D, FIG. 6E, FIG. 6F, FIG. 7A, and FIG. 8A).

With the configuration described above, the primary ion is made incident to the measurement object when the deflection unit 7 is operated by application of a predetermined voltage. Meanwhile, after the primary ion incidence, the voltage is changed from that for operating the deflection unit 7 to bring the deflection unit 7 into a non-operation state, so that it is possible to detect the secondary ion by the detector 5 through the secondary ion optical system 4 without interfering the secondary ion by the deflection unit 7. As used herein, "the voltage is changed from that for operating the deflection unit 7" includes a change of the voltage to be applied to the deflection unit to 0.

In the primary ion irradiation, a group of primary ions in a pulsed manner, i.e., a pulsed ion beam, may preferably be incident, and a beam having a diameter of 10 μm or more and 100 mm or less may preferably be incident on an emission surface of the measurement object.

Note that, in the case where it is possible to guide the secondary ion to the secondary ion detector 5 without changing the voltage to be applied to the deflection unit 7, it is possible to realize the time-of-flight mass spectrometer according to the present invention without bringing the deflection unit 7 into the non-operation state.

Although an ion optical axis 6 of the primary ion and the ion optical axis 8 of the secondary ion may be coaxially disposed (FIG. 1A) when the primary ion is made incident to the measurement object 2, it is not always necessary to dispose the ion optical axes strictly coaxially, and it is possible to dispose the axes with a shift from each other depending on an object and a situation of the measurement. When the axes are coaxially disposed, particularly, it is easy to make the primary ion perpendicularly incident to the surface of the measurement object 2, thereby the entire surface can be irradiated with the primary ion even in the case where there is irregularity on the surface of the measurement object 2. Since an ion optical axis of the secondary ion optical system 4 can also be perpendicular to the surface of the measurement object 2, simultaneously, it is possible to efficiently extract the secondary ion in a normal line direction on the surface of the measurement object 2.

As a result, a difference between a distribution of the ion emitted from the measurement object 2 and a substance distribution on the measurement object surface is improved, thereby enhancing measurement accuracy.

It should be noted that even when the ion optical axis 6 of the primary ion and the secondary ion optical axis 8 do not perfectly overlap with each other, it is possible to achieve the perpendicular incidence of the primary ion to the surface of the measurement object 2, and it is possible to irradiate the entire surface of the irregular measurement object 2 with the primary ion.

The secondary ion emitted from the measurement object 2 is accelerated by the extraction/projection electrode 3 which is a part of the secondary ion optical system 4 and, after further acceleration by a re-acceleration electrode 11 when so required, arrives at the detector 5 and detected thereby. Since a time for the secondary ion to pass through the secondary ion optical system 4 (flight time) is measured by a difference between the time when the secondary ion is emitted and the time when the secondary ion is detected, a mass (m/z) of the secondary ion is measured based on the velocity of the secondary ion.

Preferably, the detector 5 has an area sensor which detects the secondary ion to readily obtain a secondary ion mass image.

When the secondary ion optical system 4 has the property of forming a distribution image of the secondary ion emitted from a surface of the measurement object 2, the advantageous feature of being capable of measuring a substance distribution of an area irradiated with the primary ion at once is attained (so-called projection type).

Further, the secondary ion optical system 4 may more preferably have a configuration as a system having an image formation unit as a control unit such as a computer which forms a two-dimensional image based on the mass information obtained by the area sensor and a display unit such as a liquid crystal display which displays the two-dimensional image.

Also, the computer which is the control unit may form an image superimposing unit which superimposes the two-dimensional image on another two-dimensional image which is optically imaged.

Further, the mass spectrometry method of the present invention is the one for detecting a secondary ion emitted from a measurement object 2 by the detector by causing a primary ion to fly and irradiating the measurement object 2 with the primary ion, including a step of so deflecting the primary ion as to pass through between the measurement object and the detector in the course of the flight and a step of guiding the secondary ion to the detector.

Figure 5:
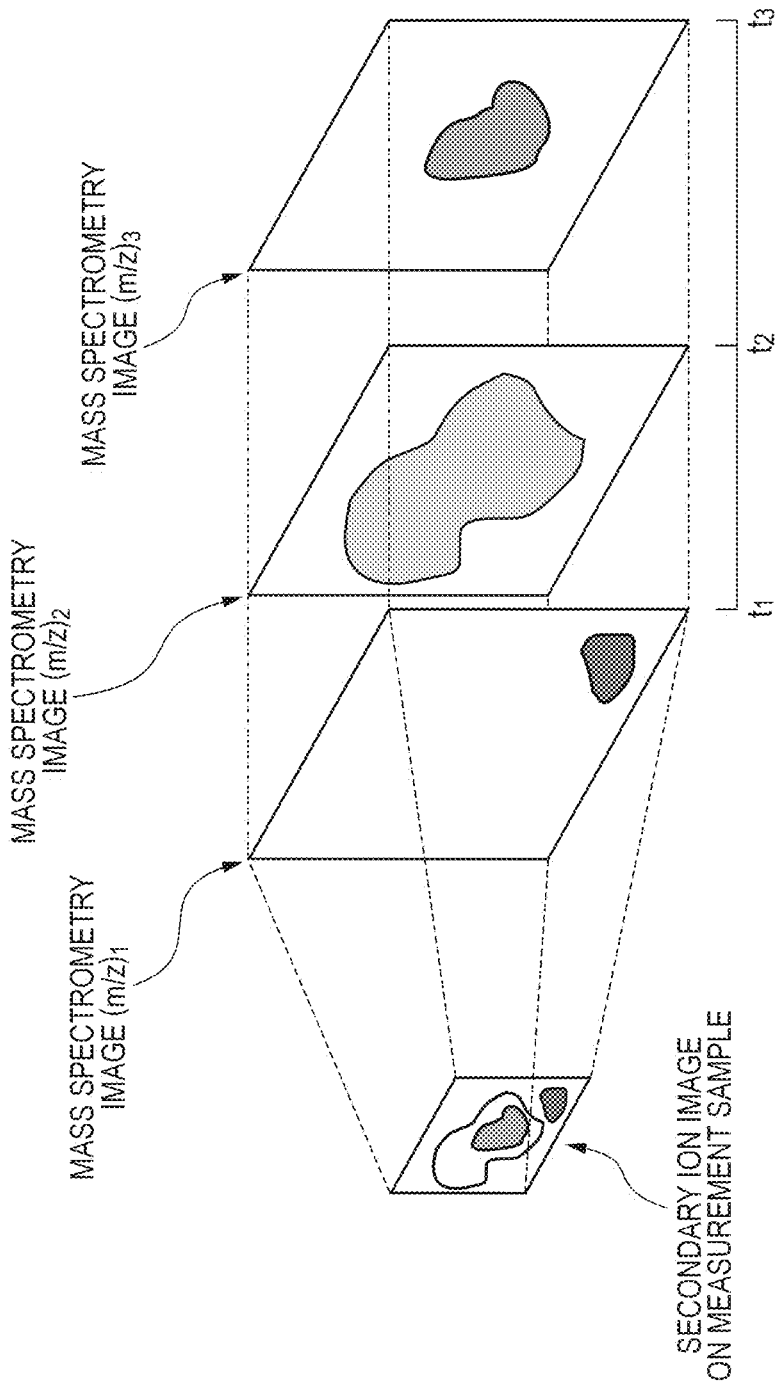
FIG. 5 is a schematic diagram showing a projection type imaging mass spectrometry.

Shown in FIG. 5 is a diagram schematically illustrating a method of performing imaging mass spectrometry depending on flight times (t1 to t3) by extracting the secondary ion as an image from the measurement object 2 by the projection type secondary ion optical system 4.

Meanwhile, when the secondary ion optical system 4 is not the projection type (FIG. 1E), it is possible to measure a substance distribution of the measurement object 2 from results of position and mass spectrometry data of fine areas by performing the mass spectrometry of the fine areas which are irradiated with a scanning primary ion beam (scanning type).

First Embodiment

Referring to FIG. 4A, a mass spectrometry method using a time-of-flight mass spectrometer (FIG. 1A) of a first embodiment will be described.

When measurement is started (A1), a voltage is applied to a parallel plate type deflection unit 7a (A2), and a primary ion is emitted from a primary ion source 1 in a pulsed manner. After a trajectory of the primary ion is deflected by the deflection unit 7a (after an incidence direction is changed), the primary ion is made incident to a measurement object 2 (A3). The deflection unit 7 of FIG. 1A has the structure of the deflection unit 7a of FIG. 3A in the present embodiment.

A primary ion trajectory 9 based on ion optical simulation is shown in FIG. 1B. The primary ion is a positive ion having acceleration energy of 10 keV, and a primary ion beam is deflected by an electric field generated between parallel plate type electrodes of the deflection unit 7a.

The deflection unit 7a of the present embodiment is formed of three or more electrodes, i.e., a main deflector electrode 70, a reference electrode 71 which is opposed to the main deflector electrode 70 with a secondary ion optical system being disposed therebetween, and an auxiliary electrode 72. At least one pair of electrodes forming the reference electrode 71 and the auxiliary electrode 72 is opposed to each other with a primary ion optical system being disposed therebetween (FIG. 3A). In FIG. 1B, voltages applied to the main deflector electrode 70, the reference electrode 71, and the auxiliary electrode 72 are 10 kV, 0 V, and 500 V, respectively.

A deflection unit 7b (FIG. 3B) having a reference electrode 73 with an aperture for allowing the primary ion to pass therethrough may be used in place of the deflection unit 7a. The deflection unit 7b is excellent in production easiness and cost due to its simple structure. However, the deflection unit 7a is used in the present embodiment since it is possible to easily adjust a position and an angle of incidence of the primary ion to the measurement object 2 in the deflection unit 7a by adjusting the voltage to be applied to the auxiliary electrode 72.

Alternatively, a quadrupolar electric field type deflection unit 7i (FIG. 3D) may be used in place of the deflection unit 7a. By applying varied voltages Vq1 and Vq2, the deflection unit 7i can deflect primary ions that flew from the direction perpendicular to the secondary ion optical axis 8 so that the primary ions can intersect a flight space of the secondary ion.

Alternatively to the above mentioned electric field type deflection units, a magnetic field type deflection unit 7c may be used. In addition, in order to adjust the primary ion incidence position, an electrode or a magnetic field application unit may be provided for deflecting the trajectory of the primary ion in a direction perpendicular to the drawing sheet in FIG. 1B.

A primary ion optical axis 6 is not parallel to a secondary ion optical axis 8 between the deflection unit 7a and the primary ion source 1, and the primary ion optical axis 6 and the secondary ion optical axis 8 are coaxial with each other at least between the measurement object 2 and an extraction/projection electrode 3 (FIG. 1B, FIG. 1C).

Since the primary ion optical axis 6 when the primary ion is made incident to the measurement object 2 is perpendicular to a surface of the measurement object or has an angle close to the perpendicular angle, irradiation of both of concave and convex portions of a surface of the measurement object 2 with the primary ion is enabled.

When the primary ion irradiation (A3) is completed, the deflection unit 7a is brought into a non-operation state (A4), and voltages are applied to the secondary ion optical system (A5). Here, when the deflection unit 7a is caused to have a potential which is identical to that of an exit side extraction/projection electrode 33, no influence is exerted on a trajectory of the secondary ion, and the secondary ion achieves uniform motion when passing through the deflection unit 7a.

In the case where it is possible to irradiate the measurement object 2 with the primary ion when the voltages are applied to the secondary ion optical system, the step of A5 may be replaced with continuous application of the voltage to the secondary ion optical system 4. The secondary ion emitted from the measurement object is accelerated by an extraction/projection electrode 3 to arrive at a detector 5 through the secondary ion optical system 4. In the present embodiment, the detector 5 is of an area sensor which detects a position of arrival of the secondary ion at the detector 5 and a time of the detection (A6). In the present embodiment, a re-acceleration electrode 11 is omitted.

In the present embodiment, the voltages applied to the electrodes, forming the extraction/projection electrode 3, are set so that the position where the secondary ion is emitted on the measurement object 2 and the position of arrival of the secondary ion at the detector 5 correspond to each other (i.e., to attain projection).

Shown in FIG. 1C are simulation results of positive secondary ion trajectories in the case where: −5 kV is applied to a main extraction/projection electrode 31; −0.7 kV is applied to a convergence extraction/projection electrode 32; −2.5 kV is applied to an exit side extraction/projection electrode 33; and −2.5 kV is applied to the detector 5. The three electrodes are aperture type electrostatic lenses having circular apertures which are coaxial to one another.

Figure 1D:
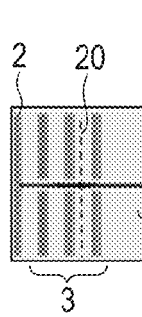
FIG. 1D is a simulation result showing secondary ion trajectories according to the first embodiment.
Figure 1E:
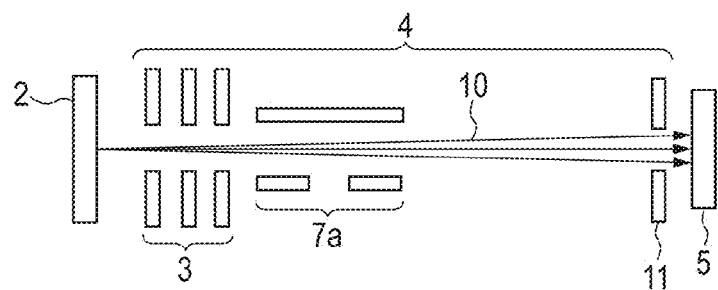
FIG. 1E is a schematic diagram showing secondary ion trajectories in a mode of embodiment of a scanning type.

The secondary ion is converged by the extraction/projection electrode 3, and an image of the secondary ion emitted from the measurement object 2 is formed in the detector 5 (FIG. 1C, FIG. 1D).

The extraction projection electrode 3 may be the aperture type electrostatic lens formed of two electrodes. The one having the three or more electrodes as described above is preferred.

A principal plane 20 of the secondary ion optical system is formed between the convergence extraction/projection electrode 32 and the exit side extraction/projection electrode 33 as shown in FIG. 1D in the present embodiment. It is possible to adjust the position of the principal plane 20 by changing the voltages applied to the main extraction/projection electrode 31, the convergence extraction/projection electrode 32, the exit side extraction/projection electrode 33, and the like.

The deflection unit 7a is positioned between the principal plane and the detector 5 in the present embodiment and, therefore, a long flight distance can be achieved during which the secondary ion is in a state of uniform motion. This is due to the fact that, since the potentials of the exit side extraction projection electrode 33 and the detector 5 are identical, the velocity of the secondary ion after passing through the extraction projection electrode 3 is not increased or decreased. Also, since the flight time t is increased when the flight distance is increased, the mass resolution is improved.

Further, as shown in the expression (1), by lengthening a distance L2 from the principal plane 20 to the detector 5 to be longer than a distance L1 from the principal plane 20 to the measurement object 2, it is possible to advantageously increase a magnification M.

$$M=L2/L1 \tag{1}$$

In FIG. 1C, the secondary ion trajectories are simulated under the conditions where L1 is 30 mm and L2 is 300 mm for the sake of simplicity of illustration, where a secondary ion image (FIG. 1D) of the measurement object 2 is projected on the detector 5 at a magnification of ×10.

It is possible to observe a finer structure of the measurement object by increasing the magnification M.

For example, when the electrodes are disposed in such a manner that L1 becomes 10 mm and L2 becomes 1000 to 3000 mm, it is possible to attain a magnification of ×100 to ×300. When a position detection resolution of the detector 5 is 10 μm, imaging mass spectrometry having spatial resolution of 0.03 to 0.1 μm is enabled.

In the present embodiment, the acceleration voltage which is smaller than that applied to the main extraction/projection electrode 31 is applied to the convergence extraction/projection electrode 32 (second electrode) which is adjacent to the main extraction/projection electrode (first electrode) 31 which is closest to the measurement object, and the acceleration voltage which is larger than that applied to the convergence extraction/projection electrode 32 is applied to the exit side extraction/projection electrode 33 (third electrode) which is adjacent to the convergence extraction/projection electrode 32.

As a result, the strong extraction electric field is produced in the vicinity of the measurement object 2 to improve detection efficiency of the secondary ion. Also, since the focus distance of the projection extraction electrode 3 is lengthened, the characteristics of the increase in magnification and the improvement in mass resolution are attained.

Also, with respect to a secondary ion having a negative electric charge, it is possible to perform mass spectrometry by reversing a polarity of a potential to be applied to the secondary ion optical system 4.

It is possible to measure the flight time t of the secondary ion by measuring a time required for the secondary ion to arrive at the detector 5 based on the time when the primary ion is made incident to the measurement object 2 (A3). In the present embodiment, since the applied voltage of the exit side extraction electrode 33 is substantially equal to the acceleration voltage $V_{ext}$ of the secondary ion at the incidence on the detector 5, it is possible to perform mass spectrometry of the secondary ion by the approximate expression (2) from the flight time t and the flight distance L of the secondary ion (A7). In the expression (2), "e" represents an elementary charge.

$$m/z=2eV_{ext}(t/L)^2 \tag{2}$$

By associating coordinates on the detector 5 with the mass spectrometry results, a mass spectrometry image (FIG. 5) of each of masses (mz) of the secondary ion is obtained (A8, A9).

Also, by adding the step of deciding a primary ion irradiation position (A10) and repeat steps A10 to A7 as shown in FIG. 4B, the mass spectrometer according to the present invention is usable as a scanning type mass spectrometer.

Second Embodiment

A mass spectrometry method using a time-of-flight mass spectrometer (FIG. 2A to FIG. 2C) of a second embodiment will be described based on FIG. 4A.

After measurement is started (A1), the flow from deflection (change of incidence direction) of a trajectory of a primary ion to incidence to a measurement object 2 (A3) is the same as the first embodiment. In the present embodiment, the deflection unit 7 of FIG. 1A has the structure of the deflection unit 7a of FIG. 3A.

Figure 2B:
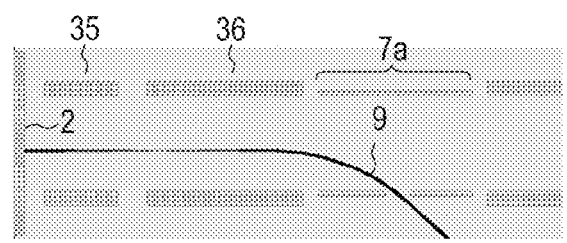
FIG. 2B is a simulation result showing primary ion trajectories simulation result according to the second embodiment.

Shown in FIG. 2B is an ion optical simulation result of primary ion trajectories 9.

The feature that a primary ion optical axis 6 and a secondary ion optical axis 8 are coaxial at least between the measurement object 2 and an extraction electrode 35 and the feature that the primary ion optical axis 6 when the primary ion is made incident to the measurement object 2 is perpendicular to a surface of the measurement object 2 or has an angle close to the perpendicular angle are the same as the first embodiment (FIG. 2A).

In the present embodiment, since the deflection unit 7a is disposed between the extraction electrode 35 and a convergence electrode 37, it is possible to dispose the deflection unit 7a closer to the measurement object 2 as compared to the first embodiment. As a result, it is possible to shorten a working distance of a primary ion source 1 to the measurement object 2.

The reduction of the working distance is advantageous when controlling the size of a primary ion beam.

When the primary ion irradiation (A3) is completed, a potential of the deflection unit 7a becomes the same as that of an intermediate electrode 36 to attain a non-operation state (A4). The timing for applying voltages to a secondary ion optical system 4 is the same as the first embodiment.

The secondary ion emitted from the measurement object 2 is accelerated via the extraction electrode 35 and the intermediate electrode 36, converged by the convergence electrode 37, and then arrives at a detector 5. Since the detector 5 is an area sensor, which detects an arrival position of the secondary ion and a time of the detection (A6), the detector 5 functions as a projection type time-of-flight mass spectrometer as is the case with the first embodiment.

Figure 2C:
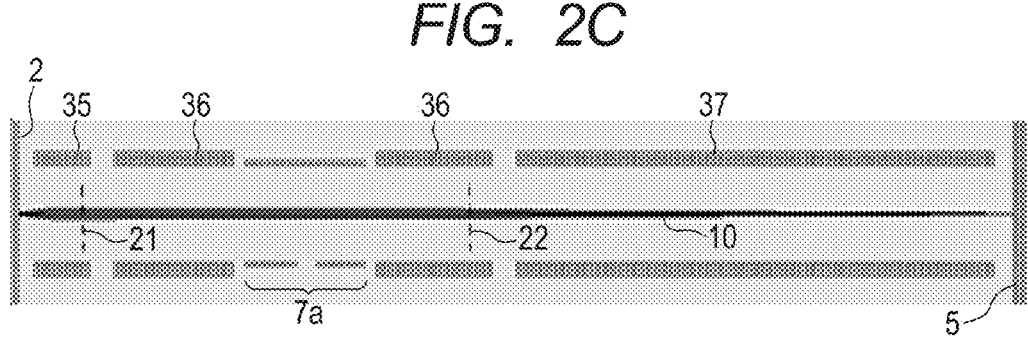
FIG. 2C is a simulation result showing secondary ion trajectories simulation result according to the second embodiment.

Shown in FIG. 2C is a simulation result of positive secondary ion trajectories in the present embodiment in the case where: −150 V is applied to the extraction electrode 35; −3.5 kV is applied to the intermediate electrode 36; −9.5 kV is applied to the convergence electrode 37; and −9.5 kV is applied to the detector 5. The three electrodes are coaxial cylindrical electrostatic lenses. Though the trajectory is different from the first embodiment, the secondary ion is converged by the convergence electrode 37, and an image of the secondary ion emitted from the measurement object 2 is formed in the secondary detector 5.

A first principal plane 21 is formed by the extraction electrode 35 and the intermediate electrode 36, and a second principal plane 22 is formed by the intermediate electrode 36 and the convergence electrode 37 (FIG. 2C). The second principal plane is positioned between the deflection unit 7a and the secondary ion detector 5. Since the positions of both of the principal planes are easily moved, adjustment of magnification is facilitated. In addition, it is possible to form a structure of having two or more principal planes by adding a principal plane by adding an electrode, and positions of the principal planes are determined depending on the positions of the electrodes and the applied voltages.

The secondary ion is efficiently detected without using the re-acceleration electrode under the conditions of FIG. 2C, since −9.5 kV is applied to the detector 5 to increase acceleration energy of the secondary ion at the incidence to the detector 5.

Since it is possible to measure a flight time t of the secondary ion based on a time when the primary ion is made incident to the measurement object 2 (A3) as in the first embodiment, it is possible to perform mass spectrometry of the secondary ion from kinetic energy of the secondary ion and a flight distance L of the secondary ion.

Since the secondary ion after passing through the principal plane 21 approximates a parallel beam when the acceleration voltage which is larger than that applied to the extraction electrode 35 is applied to the intermediate electrode 36 which is adjacent to the extraction electrode 35 which is closest to the measurement object 2 as in the present embodiment, a distance between the first principal plane 21 and the second principal plane 22 can be flexibly set. Particularly, by maintaining a distance L3 between the first principal plane 21 and the second principal plane 22 to be sufficiently larger than a distance L4 between the first principal plane 21 and the measurement object 2 and a distance L5 between the second principal plane 22 and the detector 5, it is possible to perform mass spectrometry in an approximating manner by replacing L of the expression (2) with L3 (A7).

Meanwhile, when a distance from the beginning of the convergence electrode 37 to the detector 5 is sufficiently longer than a distance from the measurement object 2 to the convergence electrode 37, it is possible to perform mass spectrometry of the secondary ion in an approximating manner by replacing $V_{ext}$ of the expression (2) with the potential of the convergence electrode 37 (A7).

On the other hand, when the distance from the convergence electrode 37 to the detector 5 is sufficiently shorter than the distance from the measurement object 2 to the convergence electrode 37, $V_{ext}$ of the expression (2) may be replaced with the potential of the extraction electrode 36.

The feature of obtaining a mass spectrometry image (FIG. 5) from the coordinates on the detector 5 and the mass spectrometry results (A8) is the same as the first embodiment.

Third Embodiment

A mass spectrometry method using a time-of-flight mass spectrometer (FIG. 6A to FIG. 6F) of a third embodiment will be described.

Figure 6A:
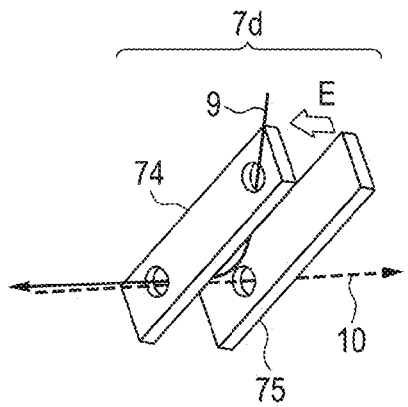
FIG. 6A is a schematic diagram showing a deflection unit according to a third embodiment.

In the present embodiment, though a penetration type deflection unit 7d of FIG. 6A is provided in place of the deflection unit 7a of the first embodiment, the feature that a primary ion is made incident to a measurement object 2 after a trajectory thereof is deflected by the penetration type deflection unit 7d, primary ion energy, a voltage applied to the extraction/projection electrode 3, and the like are the same as the first embodiment.

Figure 6B:
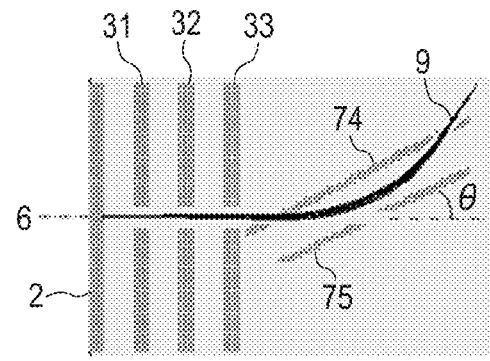
FIG. 6B is a simulation result showing primary ion trajectories simulation result according to the third embodiment.

Shown in FIG. 6B is an ion optical simulation result of primary ion trajectories 9.

In the present embodiment, the feature that a primary ion optical axis 6 and a secondary ion optical axis 8 are coaxial at least between the measurement object 2 and an extraction electrode 3 (FIG. 6B) and the feature that the primary ion optical axis 6 when the primary ion is made incident to the measurement object 2 is perpendicular to a surface of the measurement object 2 or has an angle close to the perpendicular angle are the same as the first embodiment.

In FIG. 6B, an electrode with aperture for transmission of primary ion/secondary ion 74 and an electrode with aperture for transmission of secondary ion 75 are substantially parallel to each other, and an angle θ formed with the secondary ion optical axis 8 is 30 degrees. When the primary ion is injected to the penetration type deflection unit 7d, a voltage of 0 V is applied to the former electrode, and a voltage of 3.9 kV is applied to the latter electrode. A distance between the electrodes is 9 mm. The angle θ is not always necessarily 30 degrees. However, the angle θ may preferably be satisfactory large for the primary ion trajectory 9 between an ion source 1 and the penetration type deflection unit 7d to be formed outside a secondary ion optical system 4.

When the angle θ is set to 30 degrees as in the present embodiment, the measurement object 2 can be irradiated with the focused primary ion even when the primary ion trajectory 9 has dispersion in an angular direction. Measurement accuracy is improved since a primary ion current density is increased by this feature. Also, when the characteristics are adopted to a scanning type mass spectrometer, spatial resolution can be improved.

Figure 6C:
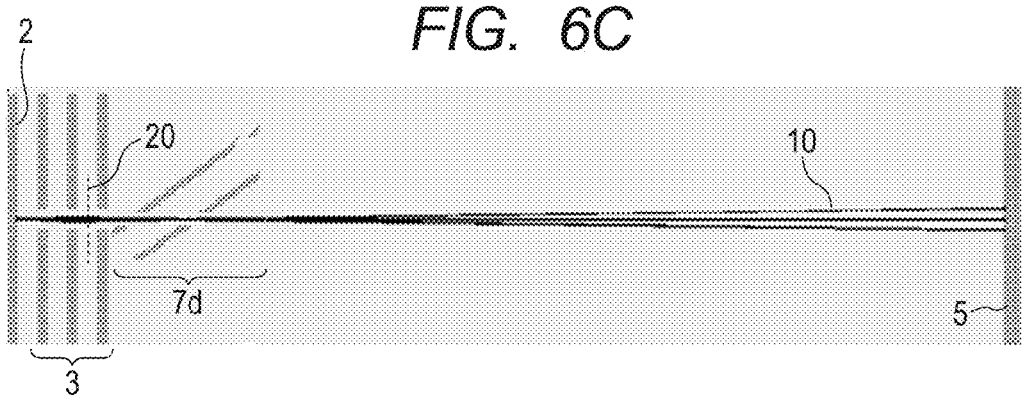
FIG. 6C is a simulation result showing secondary ion trajectories according to the third embodiment.
Figure 6D:
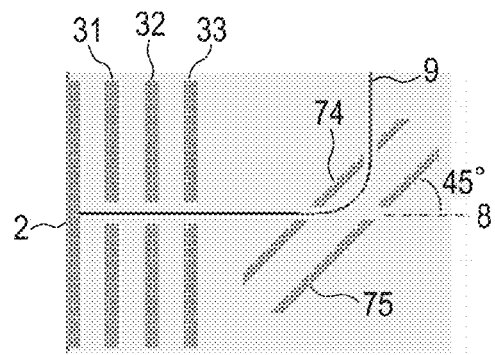
FIG. 6D is a simulation result showing primary ion trajectories simulation result when the deflection unit is of 45° type.

The angle θ may be 45 degrees as shown in FIG. 6D. With such configuration, it is possible to expect a noise reduction effect since the primary ion trajectories 9 are focused near the aperture of the electrode with aperture for transmission of primary ion/secondary ion 74 to reduce collision of the primary ion with the aperture. A voltage of 0 V is applied to the electrode with aperture for transmission of primary ion/secondary ion 74, and a voltage of 10.1 kV is applied to the electrode with aperture for transmission of secondary ion 75. A distance between the electrodes is 10 mm.

Since the convergence of the primary ion trajectory 9 relative to the angle θ continuously changes, the primary ion trajectory 9 gradually changes from the case of FIG. 6B to the case of FIG. 6D by changing the angle θ from 30 degrees to 45 degrees. Since a difference between the two angles θ is within a range of about 30%, it is possible to use the penetration type deflection unit 7d within a range of the angle θ of from 20 degrees to 60 degrees by allowing the gradual change of the convergence of the primary ion trajectory.

Figure 6E:
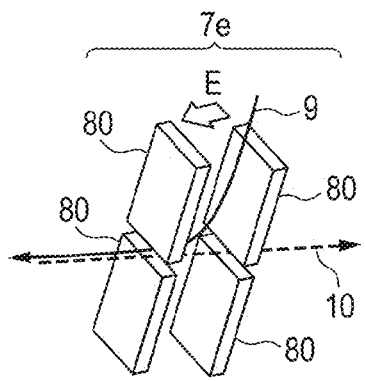
FIG. 6E is a schematic diagram showing a deflection unit of which an aperture is modified to a slit.

The aperture may not necessarily be the one having the shape of that provided in the penetration type deflection unit 7d of FIG. 6A, and an electrode 80 which has a slit for allowing the ion to pass therethrough of a penetration type deflection unit 7e of FIG. 6E may be used.

Figure 6F:
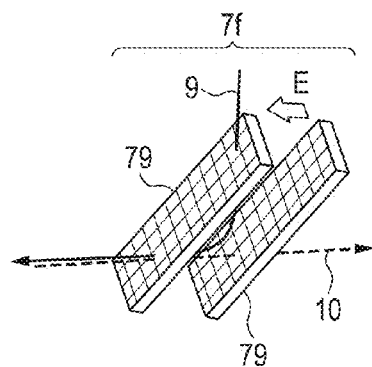
FIG. 6F is a schematic diagram showing a deflection unit using a mesh.

Further, the deflection unit 7 may be a mesh type deflection unit 7f using two mesh electrodes 79 as shown in FIG. 6F. Owing to the mesh, the deflection unit 7f allows transmission of the primary ion and the secondary ion without providing the aperture, and, therefore, disturbance of a deflection electric field which is otherwise caused by the aperture is suppressed to attain the advantage of a small fringing effect.

When the primary ion irradiation is completed, a potential of the entire deflection unit 7 (including 7d, 7e, and 7f) is changed to the potential same as that of an exit side extraction/projection electrode 33, and voltages are applied to the secondary ion optical system 4.

The secondary ion emitted from the measurement object 2 is converged by the extraction/projection electrode 3 and then arrives at a detector 5, and the detector 5 functions as an area sensor of a time-of-flight mass spectrometer as is the case with the first embodiment which enables to obtain a mass spectrometry image (FIG. 5).

Shown in FIG. 6C is a simulation result of positive secondary ion trajectories in the case where: −5 kV is applied to a main extraction/projection electrode 31; −0.7 kV is applied to a convergence extraction/projection electrode 32, −2.5 kV is applied to an exit side extraction/projection electrode 33; and −2.5 kV is applied to the detector 5.

The mass spectrometer according to the present invention is usable also as a scanning type mass spectrometer as is the case with the first embodiment. Also, the ion optical system may be formed of a coaxial cylindrical electrostatic lens in place of the aperture type electrostatic lens as in the second embodiment.

Fourth Embodiment

A mass spectrometry method using a time-of-flight mass spectrometer (FIG. 7A to FIG. 7C) of a fourth embodiment will be described.

The present embodiment is the same as the third embodiment except for using a penetration type deflection unit 7g in place of the penetration type deflection unit 7d.

Figure 7A:
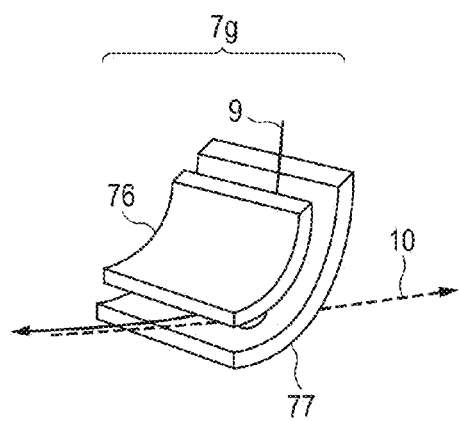
FIG. 7A is a schematic diagram showing a deflection unit according to a fourth embodiment.
Figure 7B:
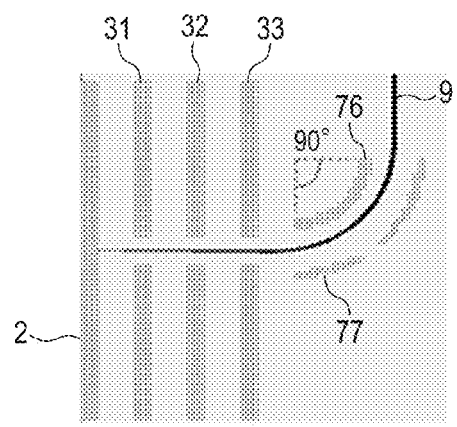
FIG. 7B is a simulation result showing primary ion trajectories simulation result according to the fourth embodiment.

Shown in FIG. 7B is an ion optical simulation result of primary ion trajectories 9 of the present embodiment.

A position relationship between a primary ion optical axis 6, a secondary ion optical axis 8, and a measurement object 2 is the same as that of the third embodiment at least between the measurement object 2 and an extraction electrode 3.

In FIG. 7B, axes of a cylindrical electrode 76 and a cylindrical electrode with aperture for transmission of secondary ion 77 are coaxial with each other, and a sector electric field is formed between the two electrodes. A center angle of the sector electric field is 90 degrees. A voltage of 0 V is applied to the former electrode, and a voltage of 8.1 kV is applied to the latter electrode. A radius of the former electrode is 14 mm, and a radius of the latter electrode is 23 mm. A distance between the electrodes is 9 mm. The center angle is not always necessarily 90 degrees. However, the center angle may preferably be satisfactory large for the primary ion trajectory 9 between an ion source 1 and the penetration type deflection unit 7g to be positioned outside a secondary ion optical system 4.

When the angle is 90 degrees as shown in FIG. 7B, the measurement object 2 is advantageously irradiated with a focused primary ion even when the primary ion trajectories 9 are spatially dispersed. Also, a center angle of 127 degrees is advantageous for converging the primary ion. The center angle may be 60 to 180 degrees from the same reasons as those of the third embodiment.

A pair of concentric spherical electrodes may be used in place of the two cylindrical electrodes.

When the primary ion irradiation is completed, a potential of the entire penetration type deflection unit 7g is changed to the potential same as that of an exit side extraction/projection electrode 33, and voltages are applied to the secondary ion optical system 4, so that a detector 5 functions as an area sensor of a projection type time-of-flight mass spectrometer as is the case with the first embodiment.

Figure 7C:
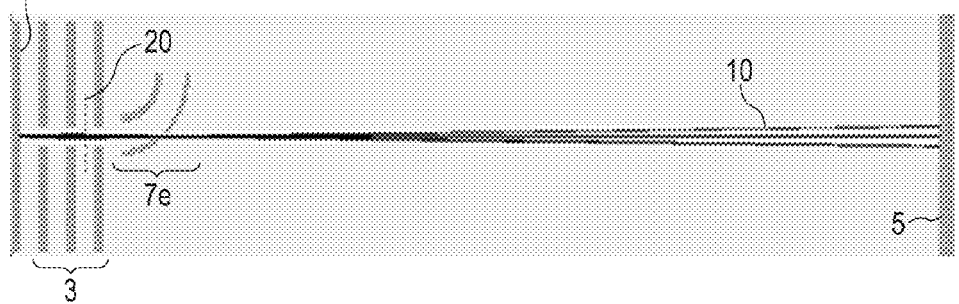
FIG. 7C is a simulation result showing a secondary ion trajectories according to the fourth embodiment.

Shown in FIG. 7C is a simulation result of positive secondary ion trajectories in the present embodiment in the case where: −5 kV is applied to a main extraction/projection electrode 31; −0.7 kV is applied to the convergence extraction electrode 32; −2.5 kV is applied to the exit side extraction/projection electrode 33; and −2.5 kV is applied to the detector 5.

The mass spectrometer according to the present invention is usable as a scanning type mass spectrometer as is the case with the first embodiment. The cylindrical electrode 76 and the cylindrical electrode with aperture for transmission of secondary ion 77 may be mesh electrodes as in the third embodiment. The ion optical system may be formed of a coaxial cylindrical electrostatic lens in place of the aperture type electrostatic lens as in the second embodiment.

Fifth Embodiment

A mass spectrometry method using a time-of-flight mass spectrometer (FIG. 8A to FIG. 8C) of a fifth embodiment will be described.

Figure 8A:
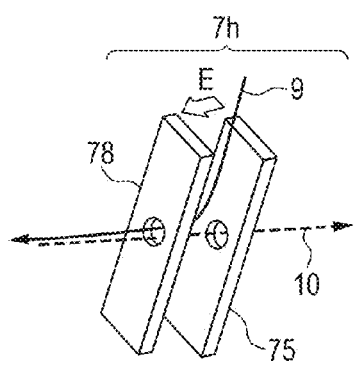
FIG. 8A is a schematic diagram showing a deflection unit according to a fifth embodiment.

The present embodiment is the same as the third embodiment except for having a deflection unit 7h shown in FIG. 8A in place of the deflection unit 7d.

Figure 8B:
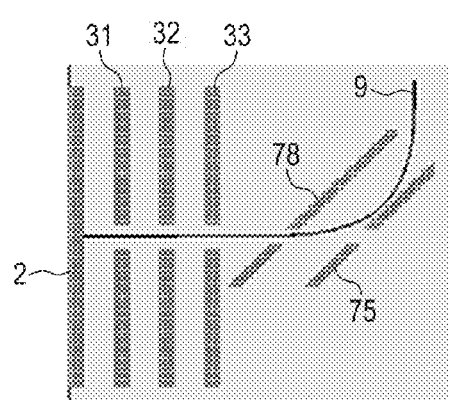
FIG. 8B is a simulation result showing primary ion trajectories simulation result according to the fifth embodiment.

Shown in FIG. 8B is an ion optical simulation result of primary ion trajectories 9. A position relationship between a primary ion optical axis 6, a secondary ion optical axis 8, and a measurement object 2 is the same as that of the third embodiment at least between the measurement object 2 and an extraction electrode 3.

The penetration type deflection unit 7h is formed of a pair of an electrode with aperture 78 and an electrode with aperture for transmission of secondary ion 75 which are substantially parallel to each other, and an angle θ relative to the secondary ion optical axis 8 is 45 degrees. When a primary ion is injected to the deflection unit 7h, a voltage of 0 V is applied to the former electrode, and a voltage of 6.2 kV is applied to the latter electrode. A distance between the electrodes is 10 mm. The inclination θ is not necessarily 45 degrees. The present embodiment has the advantages that only one aperture for transmission of the primary ion is provided to achieve the simple structure, and that a degree of freedom of a direction along which the primary ion is made incident to the penetration type deflection unit 7h is high.

When the primary ion irradiation is completed, a potential of the entire deflection unit 7 is changed to the potential same as that of an exit side extraction/projection electrode 33, and voltages are applied to the secondary ion optical system 4, so that a detector 5 functions as an area sensor of a projection type time-of-flight mass spectrometer as is the case with the first embodiment.

Figure 8C:
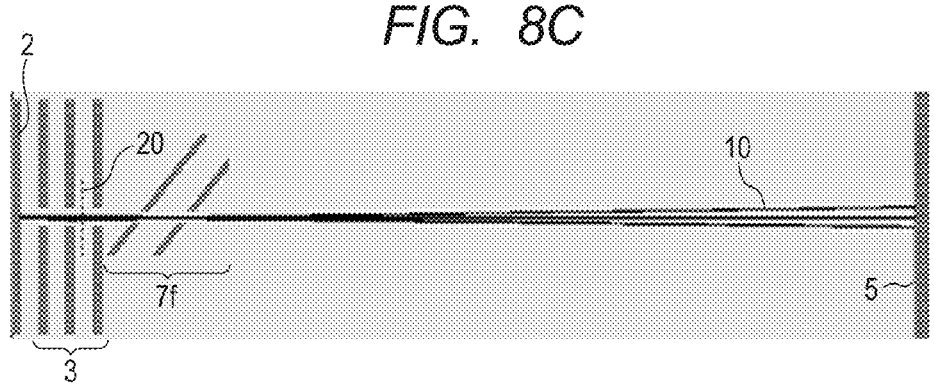
FIG. 8C is a simulation result showing secondary ion trajectories simulation result according to the fifth embodiment.

Shown in FIG. 8C is a simulation result of positive secondary ion trajectories in the present embodiment in the case where: −5 kV is applied to a main extraction/projection electrode 31; −0.7 kV is applied to a convergence extraction electrode 32; −2.5 kV is applied to the exit side extraction/projection electrode 33; and −2.5 kV is applied to the detector 5.

The mass spectrometer according to the present invention is usable as a scanning type mass spectrometer as is the case with the first embodiment. The electrode with aperture 78 and the electrode with aperture for transmission of secondary ion 75 may be mesh electrodes as in the third embodiment. The ion optical system may be formed of a coaxial cylindrical electrostatic lens in place of the aperture type electrostatic lens as in the second embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-225509, filed Oct. 13, 2011, and Japanese Patent Application No. 2012-223084, filed Oct. 5, 2012, which are hereby incorporated by reference herein in their entirety.

The invention claimed is:

1. A mass spectrometer comprising:
  a platform on which a measurement object is placed;
  a primary ion generator configured to generate a primary ion to be flown;
  a primary ion optical system configured to guide the primary ion to the measurement object and irradiate the measurement object with the primary ion;
  a detection unit configured to detect a secondary ion emitted from the measurement object; and
  a secondary ion optical system configured to guide the secondary ion to the detection unit;
  wherein the primary ion optical system includes a deflection unit configured to deflect the primary ion in such a manner that the primary ion intersects a flight space of the secondary ion in the course of flight.

2. The mass spectrometry device according to claim 1, wherein the primary ion flies in such a manner that the primary ion is deflected by the deflection unit from outside of a flight space of the secondary ion to inside of the flight space.

3. The mass spectrometer according to claim 1, wherein an ion optical axis of the primary ion optical system is coaxial with the ion optical axis of the secondary ion optical system at least when the primary ion is made incident to the measurement object.

4. The mass spectrometer according to claim 1, wherein the deflection unit deflects a trajectory of the primary ion by an electric field.

5. The mass spectrometer according to claim 4, wherein the deflection unit includes two or more electrodes.

6. The mass spectrometer according to claim 5, wherein at least a pair of the electrodes are opposed to each other with an ion optical axis of the secondary ion optical system being disposed therebetween, and
  wherein potentials applied to the electrodes opposed to each other with the ion optical axis of the secondary ion optical system being disposed therebetween are varied from each other.

7. The mass spectrometer according to claim 5, wherein at least one pair of electrodes are opposed to each other with the trajectory of the primary ion being disposed therebetween, and
  wherein potentials applied to the electrodes opposed to each other with the trajectory of the primary ion optical system being disposed therebetween are varied from each other.

8. The mass spectrometer according to claim 5, wherein one of the two or more electrodes has:
  a first electrode which has an aperture for allowing at least one of the primary ion and the secondary ion to pass therethrough; and
  a second electrode.

9. The mass spectrometer according to claim 8, wherein the aperture of the first electrode allows only the primary ion to pass therethrough.

10. The mass spectrometer according to claim 8, wherein at least one of the first electrode and the second electrode is inclined from the ion optical axis of the secondary ion optical system, and
  wherein one of the two or more electrodes has:
    a first electrode which has an aperture for allowing at least one of the primary ion and the secondary ion to pass therethrough; and
    a second electrode which has an aperture for allowing the secondary ion to pass therethrough.

11. The mass spectrometer according to claim 10, wherein the first electrode has a plurality of apertures, and
  wherein more than two of the apertures of the first electrode allow the first ion to pass therethrough.

12. The mass spectrometer according to claim 8, wherein the first electrode and the second electrode form a sector electric field.

13. The mass spectrometer according to claim 12, wherein a center angle of the sector electric field is 90 degrees to 127 degrees.

14. The mass spectrometer according to claim 8, wherein at least one of the first electrode and the second electrode is a mesh electrode.

15. The mass spectrometer according to claim 8, wherein at least one of the aperture of the first electrode and the aperture of the second electrode is a slit for allowing the ion to pass therethrough.

16. The mass spectrometer according to claim 10, wherein at least one of the first electrode and the second electrode is inclined at from 30 degrees to 45 degrees from the ion optical axis of the secondary ion optical system.

17. The mass spectrometer according to claim 1, wherein the deflection unit deflects the trajectory of the primary ion by a magnetic field.

18. The mass spectrometer according to claim 1, wherein the device is a time-of-flight mass spectrometer.

19. The mass spectrometer according to claim 1, wherein the primary ion generator is disposed outside an ion optical axis of the secondary ion optical system, and
  wherein the deflection unit is formed between the measurement object and the detection unit.

20. The mass spectrometer according to claim 19, wherein the deflection unit is disposed between a principal plane of the secondary ion optical system and the detection unit.

21. The mass spectrometer according to claim 19, wherein the secondary ion optical system has two or more principal planes, and
  wherein the deflection unit is positioned between at least one of the principal planes and the measurement object.

22. The mass spectrometer according to claim 1, wherein the secondary ion optical system includes a directing unit configured to direct the emitted secondary ion to the detection unit, and
  wherein the directing unit is disposed in such a manner as to enclose a flight space of the secondary ion.

23. The mass spectrometer according to claim 22, wherein the secondary ion includes two or more electrodes, and
  wherein an acceleration voltage which is larger than a voltage applied to a first electrode is applied to a second electrode which is placed on a different side, of the first electrode, from the measurement object.

24. The mass spectrometer according to claim 22, wherein the secondary ion optical system includes three or more electrodes,
  wherein an acceleration voltage which is smaller than a voltage applied to a first electrode is applied to a second electrode which is placed on a different side, of the first electrode, from the measurement object, and
  wherein an acceleration voltage which is larger than the voltage applied to the second electrode is applied to a third electrode which is placed on a different side, of the second electrode, from the first electrode.

25. The mass spectrometer according to claim 1, wherein the primary ion generator irradiates a emission surface of the measurement object with a beam having a diameter of 10 μm or more and 100 mm or less.

26. The mass spectrometer according to claim 1, wherein the secondary ion optical system is of a projection type.

27. The mass spectrometer according to claim 26, wherein the detection unit includes an area sensor configured to detect the secondary ion.

28. The mass spectrometer according to claim 27, further comprising an image forming unit configured to form a two-dimensional image based on mass information obtained by the area sensor.

29. The mass spectrometer according to claim 28, further comprising a display unit configured to display the two-dimensional image.

30. The mass spectrometer according to claim 29, further comprising an image superimposing unit configured to superimpose the two-dimensional image onto another two-dimensional image which is optically imaged.

31. A mass spectrometry method for causing a primary ion to fly, irradiating a measurement object with the primary ion, and detecting a secondary ion emitted from the measurement object by a detector, comprising:

deflecting the primary ion in such a manner that the primary ion intersects between the measurement object and the detector in the course of flight and intersects a flight space of the secondary ion in the course of flight; and guiding the secondary ion to the detector.

\* \* \* \* \*